(12) United States Patent
Esler

(10) Patent No.: US 6,754,534 B2
(45) Date of Patent: Jun. 22, 2004

(54) CARDIAC RHYTHM MANAGEMENT SYSTEM WITH PREVENTION OF DOUBLE COUNTING OF EVENTS

(75) Inventor: James A. Esler, New Brighton, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/801,295

(22) Filed: Mar. 7, 2001

(65) Prior Publication Data

US 2001/0041919 A1 Nov. 15, 2001

Related U.S. Application Data

(62) Division of application No. 09/294,725, filed on Apr. 19, 1999, now Pat. No. 6,240,313.

(51) Int. Cl.$^7$ ................................................. A61N 1/08
(52) U.S. Cl. ........................................................ 607/27
(58) Field of Search ................................ 600/509, 515, 600/516, 518, 519; 607/4, 5, 9, 14, 15, 25, 28

(56) References Cited

U.S. PATENT DOCUMENTS

| | | | |
|---|---|---|---|
| 3,707,959 A | 1/1973 | Wilton-Davies | 128/2.06 A |
| 3,768,486 A | 10/1973 | Berkovitis | 128/419 P |
| 3,952,731 A * | 4/1976 | Worstencroft | |
| 4,250,883 A | 2/1981 | Thompson | 128/419 PG |
| 4,276,883 A | 7/1981 | McDonald et al. | 128/419 PT |
| 4,401,120 A | 8/1983 | Hartlaub et al. | 128/419 PT |
| 4,493,325 A * | 1/1985 | Hartlaub et al. | 128/419 PG |
| 4,498,478 A | 2/1985 | Bourgeois | 128/419 PG |
| 4,515,159 A | 5/1985 | McDonald et al. | 128/419 PG |
| 4,549,548 A | 10/1985 | Wittkampf et al. | 128/419 PG |
| 4,561,442 A * | 12/1985 | Vollmann et al. | 128/419 PG |
| 4,712,554 A | 12/1987 | Garson, Jr. | 128/419 PG |
| 4,928,688 A | 5/1990 | Mower | 128/419 PG |
| 5,042,480 A | 8/1991 | Hedin et al. | 128/419 PG |
| 5,085,215 A * | 2/1992 | Nappholz et al. | 1128/419 PG |
| 5,161,527 A | 11/1992 | Nappholz et al. | 128/419 PG |
| 5,183,040 A | 2/1993 | Nappholz et al. | 128/419 PG |
| 5,184,615 A | 2/1993 | Nappholz et al. | 128/419 PG |
| 5,193,535 A | 3/1993 | Bardy et al. | 128/419 D |

(List continued on next page.)

FOREIGN PATENT DOCUMENTS

| | | | |
|---|---|---|---|
| EP | 0879620 | 11/1998 | A61N/1/368 |
| WO | 97/39799 | 10/1997 | A61N/1/362 |

*Primary Examiner*—Jeffrey R. Jastrzab
*Assistant Examiner*—Frances P. Oropeza
(74) *Attorney, Agent, or Firm*—Schwegman, Lundberg, Woessner & Kluth, P.A.

(57) ABSTRACT

A cardiac rhythm management system recognizes patterns of interval durations, distinguishing between events in different heart chambers even though signals associated with those different heart chambers are processed using a commonly shared sensing circuit. A therapy delivery algorithm ignores intervals between cardiac events occurring in different heart chambers when determining a cardiac rate upon which the delivery of therapy is based. This reduces the risk of inappropriate delivery of therapy to the patient. Delayed conduction left ventricular beats are not erroneously recognized as a subsequent right ventricular beat, preventing such short intervals from inappropriately triggering a defibrillation countershock. The system detects cardiac events, obtains a current interval between a current cardiac event and a previous cardiac event, and classifies the current interval into at least first and second categories, based on a duration of the current interval. The system determines timing of delivery of output energy based on whether a previous interval is in the first category and the current interval is in the second category. The system then stores the current interval as the previous interval.

7 Claims, 7 Drawing Sheets

U.S. PATENT DOCUMENTS

| | | | |
|---|---|---|---|
| 5,257,621 A | 11/1993 | Bardy et al. | 607/5 |
| 5,267,559 A | 12/1993 | Jin et al. | 128/419 D |
| 5,271,394 A | 12/1993 | Girodo et al. | 607/15 |
| 5,312,445 A | 5/1994 | Nappholz et al. | 607/9 |
| 5,330,508 A * | 7/1994 | Gunderson | 607/14 |
| 5,366,486 A * | 11/1994 | Zipes et al. | 607/5 |
| 5,447,519 A | 9/1995 | Peterson | 607/5 |
| 5,454,836 A | 10/1995 | van der Veen et al. | 607/9 |
| 5,514,161 A | 5/1996 | Limousin | 607/9 |
| 5,522,852 A | 6/1996 | White et al. | 607/5 |
| 5,545,186 A | 8/1996 | Olson et al. | 607/14 |
| 5,549,649 A | 8/1996 | Florio et al. | 607/15 |
| 5,658,320 A | 8/1997 | Betzold et al. | 607/14 |
| 5,672,170 A | 9/1997 | Cho et al. | 606/12 |
| 5,676,686 A | 10/1997 | Jensen et al. | 607/9 |
| 5,683,431 A | 11/1997 | Wang | 607/28 |
| 5,755,736 A * | 5/1998 | Gillberg et al. | 607/4 |
| 5,755,737 A | 5/1998 | Prieve et al. | 607/4 |
| 5,755,739 A | 5/1998 | Sun et al. | 607/14 |
| 5,759,196 A | 6/1998 | Hess et al. | 607/14 |
| 5,766,232 A | 6/1998 | Grevious et al. | 607/60 |
| 5,776,168 A | 7/1998 | Gunderson | 607/27 |
| 5,788,717 A | 8/1998 | Mann et al. | 607/14 |
| 5,836,975 A | 11/1998 | DeGroot | 607/5 |
| 5,846,263 A | 12/1998 | Peterson et al. | 607/14 |
| 5,855,593 A | 1/1999 | Olson et al. | 607/9 |
| 5,867,386 A | 2/1999 | Hoffberg et al. | 364/188 |
| 5,885,221 A | 3/1999 | Hsu et al. | 600/515 |
| 5,893,882 A | 4/1999 | Peterson et al. | 607/14 |
| 5,931,857 A | 8/1999 | Prieve et al. | 607/14 |
| 5,951,592 A * | 9/1999 | Murphy | 607/4 |
| 5,951,593 A | 9/1999 | Lu et al. | 607/14 |
| 5,956,272 A | 9/1999 | Roohparvar | 365/185.19 |
| 5,978,704 A * | 11/1999 | Ideker et al. | 607/5 |
| 5,978,707 A | 11/1999 | Krig et al. | 607/14 |
| 5,987,356 A | 11/1999 | DeGroot | 607/5 |
| 5,991,657 A | 11/1999 | Kim | 607/5 |
| 5,999,850 A | 12/1999 | Dawson et al. | 607/4 |
| 6,061,592 A * | 5/2000 | Nigam | 600/518 |
| 6,129,745 A * | 10/2000 | Sun et al. | 607/27 |

* cited by examiner

CARDIAC RHYTHM MANAGEMENT SYSTEM WITH PREVENTION OF DOUBLE COUNTING OF EVENTS

CROSS REFERENCE TO RELATED APPLICATIONS

This application is a division of U.S. patent application Ser. No. 09/294,725, filed on Apr. 19, 1999 now U.S. Pat. No. 6,240,313, the specification of which is incorporated herein by reference.

TECHNICAL FIELD

This invention relates generally to cardiac rhythm management systems and particularly, but not by way of limitation, to a cardiac rhythm management system that prevents double counting of one or more of intrinsic or paced events.

BACKGROUND

When functioning properly, the human heart maintains its own intrinsic rhythm, and is capable of pumping adequate blood throughout the body's circulatory system. However, some people have irregular cardiac rhythms, referred to as cardiac arrhythmias. Such arrhythmias result in diminished blood circulation. One mode of treating cardiac arrhythmias uses drug therapy. Drugs are often effective at restoring normal heart rhythms. However, drug therapy is not always effective for treating arrhythmias of certain patients. For such patients, an alternative mode of treatment is needed. One such alternative mode of treatment includes the use of a cardiac rhythm management system. Such systems are often implanted in the patient and deliver therapy to the heart.

Cardiac rhythm management systems include, among other things, pacemakers, also referred to as pacers. Pacers deliver timed sequences of low energy electrical stimuli, called pace pulses, to the heart, such as via a transvenous leadwire or catheter (referred to as a "lead") having one or more electrodes disposed in or about the heart. Heart contractions are initiated in response to such pace pulses (this is referred to as "capturing" the heart). By properly timing the delivery of pace pulses, the heart can be induced to contract in proper rhythm, greatly improving its efficiency as a pump. Pacers are often used to treat patients with bradyarrhythmias, that is, hearts that beat too slowly, or irregularly.

Cardiac rhythm management systems also include cardioverters or defibrillators that are capable of delivering higher energy electrical stimuli to the heart. Defibrillators are often used to treat patients with tachyarrhythmias, that is, hearts that beat too quickly. Such too-fast heart rhythms also cause diminished blood circulation because the heart isn't allowed sufficient time to fill with blood before contracting to expel the blood. Such pumping by the heart is inefficient. A defibrillator is capable of delivering an high energy electrical stimulus that is sometimes referred to as a defibrillation countershock. The countershock interrupts the tachyarrhythmia, allowing the heart to reestablish a normal rhythm for the efficient pumping of blood. In addition to pacers, cardiac rhythm management systems also include, among other things, pacer/defibrillators that combine the functions of pacers and defibrillators, drug delivery devices, and any other systems or devices for diagnosing or treating cardiac arrhythmias.

One problem faced by cardiac rhythm management systems is the treatment of congestive heart failure (also referred to as "CHF"). Congestive heart failure, which can result from long-term hypertension, is a condition in which the walls of at least one side (e.g., the left side) of the heart become thin. As a result, the left atrium and left ventricle become disproportionately enlarged. The heart muscle associated with the left atrium and ventricle displays less contractility. This decreases cardiac output of blood through the circulatory system which, in turn, may result in an increased heart rate and less resting time between heartbeats. The heart consumes more energy and oxygen, and its condition typically worsens over a period of time.

As one side of the heart (e.g., the left side) becomes disproportionately enlarged, the intrinsic electrical heart signals that control heart rhythm are also affected. Normally, such intrinsic signals originate in the sinoatrial (SA) node in the upper right atrium, traveling through and depolarizing the atrial heart tissue such that resulting contractions of the right and left atria are triggered. The intrinsic atrial heart signals are received by the atrioventricular (AV) node which, in turn, triggers a subsequent ventricular intrinsic heart signal that travels through and depolarizes the ventricular heart tissue such that resulting contractions of the right and left ventricles are triggered substantially simultaneously.

Where one side (e.g., the left side) of the heart has become disproportionately enlarged due to congestive heart failure, however, the ventricular intrinsic heart signals may travel through and depolarize the left side of the heart more slowly than in the right side of the heart. As a result, the left and right ventricles do not contract simultaneously, but rather, the left ventricle contracts after the right ventricle. This delay between right ventricular and left ventricular contractions reduces the pumping efficiency of the heart due to movement of the septal wall between right and left sides of the heart. Congestive heart failure may also result in an another symptom, that is, an overly long delay between atrial and ventricular contractions. This too-long delay between atrial and ventricular contractions also reduces the pumping efficiency of the heart. There is a need to provide congestive heart failure patients with therapy that improves heart pumping efficiency.

Conventional cardiac rhythm management techniques, however, are typically directed toward treating the right side of the heart, which pumps blood to the lungs. For example, endocardial leads are typically designed to be inserted via the superior vena cava into one or more of the right atrium and right ventricle. Because the left side of the heart pumps blood throughout the patient's peripheral circulatory system, pressures are typically higher in the left side of the heart than on the right side of the heart. Because access to the left side of the heart is more difficult, and because a thrombus forming on a left side lead could cause a stroke or a myocardial infarction, it is typically very difficult to chronically implant an endocardial catheter leads directly into the left atrium and left ventricle of the heart.

Another problem with treating congestive heart failure patients involves sensing intrinsic heart signals. Cardiac rhythm management devices typically sense intrinsic atrial and ventricular heart signals, and adjust the therapy being delivered to the heart based at least in part on events detected from these sensed signals or from the delivery of the therapy itself. Such events are also referred to as "beats," "activations," "depolarizations," or "contractions," and are sensed via one or more electrodes located at or near that portion of the heart from which the sensed signals are to be obtained. Atrial depolarizations are also referred to as "P-waves." Ventricular depolarizations are also referred to as "QRS complexes," or "R-waves." Congestive heart failure, however, may result in a significant delay between right and left ventricular contractions, as discussed above. Such delays not only decrease the pumping efficiency of the heart, they may also result in the sensing of a right ventricular depolarization that is separated in time from a sensed left ventricular depolarization.

In order to properly deliver therapy to the heart based on sensed events, the cardiac rhythm management system must be able to distinguish between sensed right and left ventricular depolarizations that are separated in time because of delayed conduction through an enlarged left ventricle, and successive depolarizations originating in the same heart chamber that represent successive contractions of the same heart chamber. For example, if the cardiac rhythm management system mistakenly recognizes a right ventricular depolarization followed shortly by a left ventricular depolarization as a pair of successive right ventricular depolarizations, then therapy (such as, for example, a defibrillation countershock) may be delivered inappropriately, particularly if this behavior is sensed repeatedly over several cardiac cycles. Because defibrillation countershocks are typically quite painful to the patient and may further irritate the heart, the inappropriate delivery of defibrillation countershocks should be avoided, if possible. Similarly, therapy (such as, for example, a pacing stimulus) may be inappropriately withheld (i.e., "inhibited") because the left ventricular depolarization is mistaken for a subsequent right ventricular depolarization. There is a need for improved sensing and event recognition techniques that reduce the likelihood that left ventricular depolarizations are mistakenly recognized as right ventricular depolarizations (or vice-versa) so that the cardiac rhythm management system can provide appropriate therapy to the patient based on sensed events.

SUMMARY

This document discloses, among other things, a cardiac rhythm management system that recognizes patterns of interval durations, allowing it to distinguish between events occurring in different heart chambers, even though signals associated with those different heart chambers are processed using a commonly shared sensing circuit. The pattern recognition techniques allow the therapy delivery algorithms to ignore intervals between cardiac events occurring in different heart chambers when determining a cardiac rate upon which the delivery of therapy is based. This reduces the risk of inappropriate delivery of therapy to the patient. For example, delayed conduction left ventricular beats are not erroneously recognized as a subsequent right ventricular beat, preventing such short intervals from inappropriately triggering a defibrillation countershock.

One aspect of the present system includes a method. The system detects cardiac events. The system obtains a current interval between a current cardiac event and a previous cardiac event. The system classifies the current interval into at least first and second categories, based on a duration of the current interval. The system determines timing of the delivery of output energy based on whether a previous interval is in the first category and the current interval is in the second category. The system then stores the current interval as the previous interval.

In one embodiment, the system includes a first sensing circuit, adapted for being coupled to first and second leads for sensing heart signals from respective first and second heart chambers. A therapy circuit is adapted for being coupled to the first and second leads for delivering therapy to the respective first and second heart chambers. A controller controls delivery of therapy by the therapy circuit based at least in part on signals received by the first sensing circuit. The controller includes a classification module, classifying previous and current intervals between cardiac events based on duration. The controller also includes a pattern recognition module, recognizing patterns in the current and previous intervals based on their classification. The controller further includes a therapy delivery control module, controlling delivery of therapy based the intervals between cardiac events, and ignoring the current interval based on a classification of the current and previous intervals. Other aspects of the invention will be apparent on reading the following detailed description of the invention and viewing the drawings that form a part thereof.

BRIEF DESCRIPTION OF THE DRAWINGS

In the drawings, like numerals describe substantially similar components throughout the several views. Like numerals having different letter suffixes represent different instances of substantially similar components.

DETAILED DESCRIPTION

Figure 1:
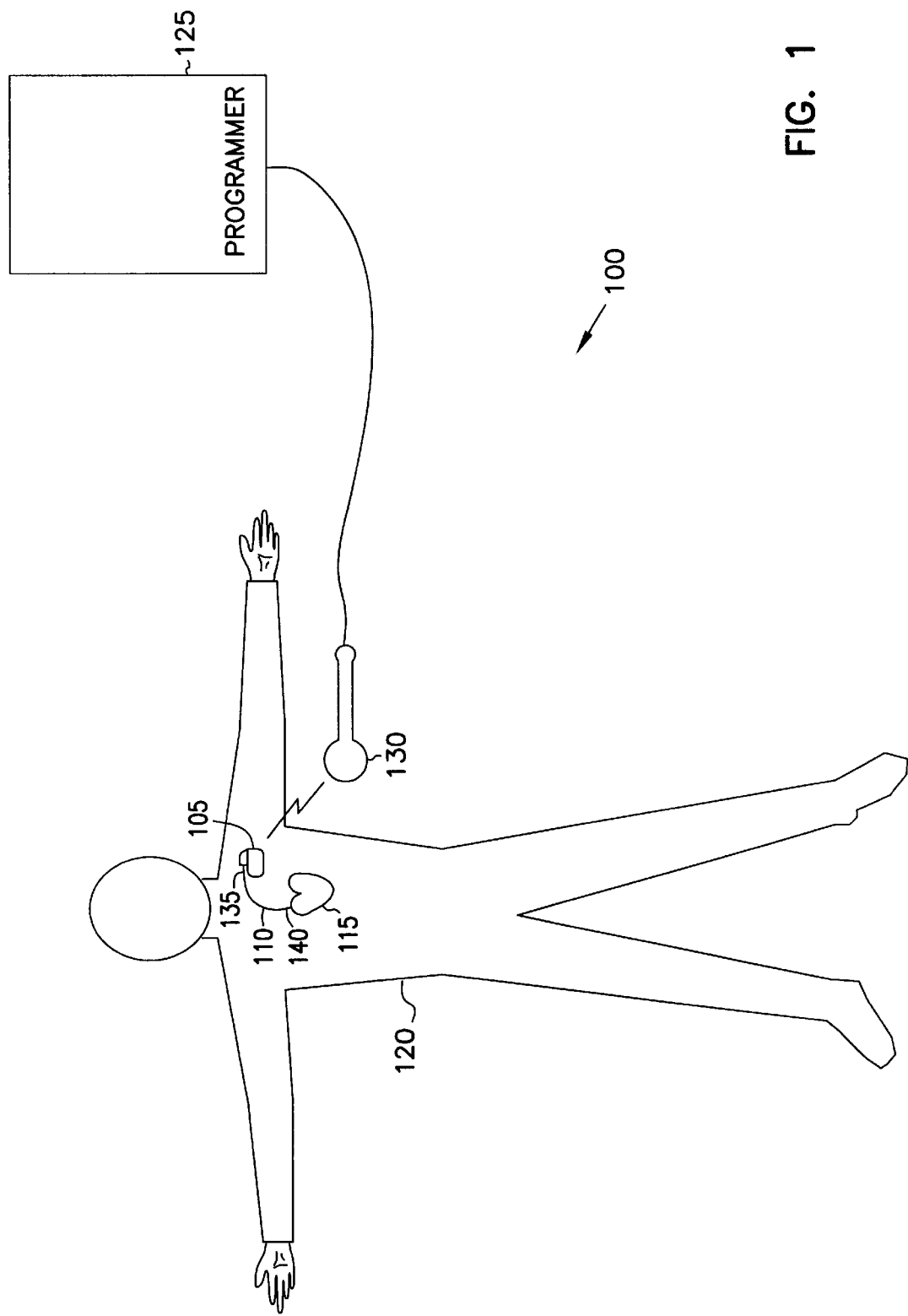
FIG. 1 is a schematic drawing illustrating one embodiment of portions of a cardiac rhythm management system and an environment in which it is used.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description is, therefore, not to be taken in a limiting sense, and the scope of the present invention is defined by the appended claims and their equivalents. In the drawings, like numerals describe substantially similar components throughout the several views. Like numerals having different letter suffixes represent different instances of substantially similar components.

General System Overview and Examples

This document describes, among other things, a cardiac rhythm management system that provides improved sensing and event recognition techniques. The techniques disclosed in this document reduce the likelihood that left side depolarizations, for example, are mistakenly recognized as right side depolarizations (or vice-versa). As a result, the present cardiac rhythm management system can provide more appropriate therapy to the patient based on sensed events.

FIG. 1 is a schematic drawing illustrating, by way of example, but not by way of limitation, one embodiment of portions of a cardiac rhythm management system 100 and an environment in which it is used. In FIG. 1, system 100 includes an implantable cardiac rhythm management device 105, also referred to as an electronics unit, which is coupled by an intravascular endocardial lead 110, or other lead, to a heart 115 of patient 120. System 100 also includes an external or other remote programmer 125 providing wireless communication with device 105 using a telemetry device 130. Catheter lead 110 includes a proximal end 135, which is coupled to device 105, and a distal end 140, which is coupled to one or more portions of heart 115.

Figure 2:
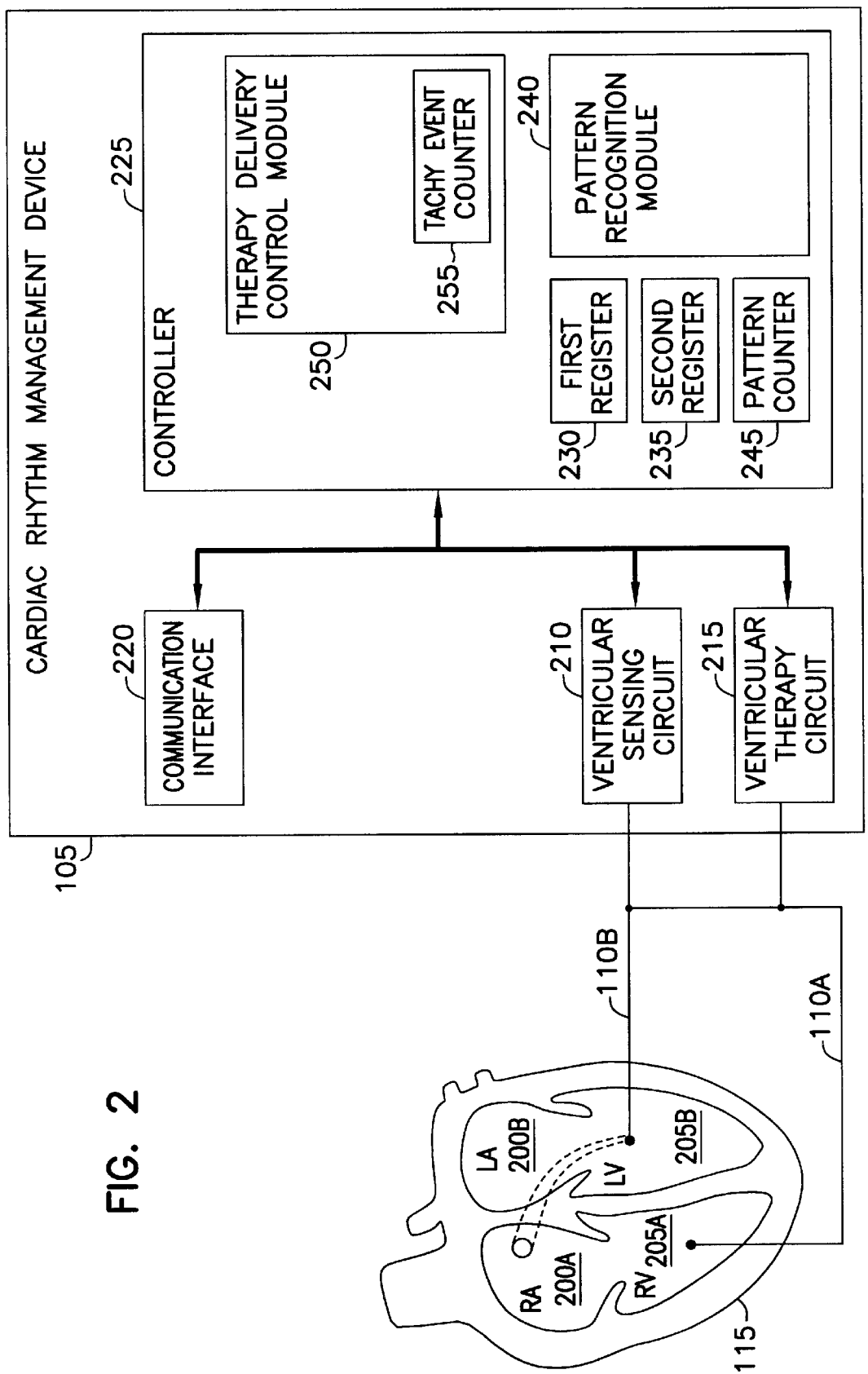
FIG. 2 is a schematic drawing illustrating generally one embodiment of portions of a cardiac rhythm management device coupled by leads to a heart.

FIG. 2 is a schematic drawing illustrating generally, by way of example, but not by way of limitation, one embodiment of portions of device 105 coupled by leads 110A–B to heart 115, which includes a right atrium 200A, a left atrium 200B, a right ventricle 205A, a left ventricle 205B, and a coronary sinus 220 extending from right atrium 200A. In this embodiment, right ventricular lead 110A includes one or more electrodes (electrical contacts) disposed in, around, or near right ventricle 205A of heart 115, such as one or more of a ring, tip, coil, or other electrode, for sensing signals or delivering one or more of pacing, defibrillation, countershock, cardioversion, or anti-tachyarrhythmia pacing (ATP) therapy to right ventricle 205A.

In FIG. 2, a left ventricular lead 110B includes one or more electrodes disposed in, around, or near left ventricle 205B of heart 115, such as one or more of a ring, tip, coil or other electrode, for sensing signals or delivering one or more of pacing, defibrillation countershock, cardioversion, or anti-tachyarrhythmia pacing therapy to left ventricle 205B. Device 105 includes components that are enclosed in a hermetically-sealed can. Additional electrodes may be located on the can, or on an insulating header, or on other portions of device 105, for providing one or more of unipolar or bipolar pacing or defibrillation energy in conjunction with the electrodes disposed on or around heart 115. Other forms of electrodes include meshes, patches, and screw-in tips which may be applied to endocardial or epicardial portions of heart 115 or which may be implanted in other areas of the body to help "steer" electrical currents produced by device 105. The present method and apparatus will work in a variety of configurations and with a variety of electrical contacts or "electrodes."

FIG. 2 illustrates a single-channel embodiment in which at least one conductor of right ventricular lead 110A is electrically coupled to at least one conductor of left ventricular lead 110B, such that electrodes associated with right ventricle 205A and left ventricle 205B share a common ventricular sensing circuit 210 and a common ventricular therapy circuit 215. Variations of the illustrated single-channel embodiment include other channels (e.g., associated with other heart chambers), but at least one of the channels is coupled to electrodes at two different locations, such as within two different chambers of heart 115. In one example, leads 110A–B are implemented as a single lead that is bifurcated to allow disposition of electrodes at different locations, such as associated with two different chambers of heart 115. In another example, leads 110A and 110B are separate leads that are received at receptacles at a header portion of device 105, but at least one conductor of lead 110A is electrically coupled to at least one conductor of lead 110B within the header or elsewhere in device 105, or using an adapter located in the lead 110. In one embodiment, right ventricular lead 110A is an intravascular endocardial lead with an electrode disposed near the apex of right ventricle 205A, and left ventricular lead 110B is an epicardial lead with a screw-in or other electrode associated with left ventricle 205B. In another embodiment, however, left ventricular lead 110B is an intravascular endocardial lead that introduced into the coronary sinus 220. This lead 110B is then extended into the great cardiac vein such that an intravascular electrode is associated with tissue of left ventricle 205B.

In FIG. 2, device 105 also includes a communication interface 220, such as a circuit for communicating with remote programmer 125 via telemetry device 130. Ventricular sensing circuit 210 receives intrinsic heart signals from leads 110A–B, but because the conductors of leads 110A–B are electrically intercoupled, sensing circuit 210 receives no other independent information regarding the chamber in which the sensed signals originated. Controller 225 includes one or more of hardware modules, software modules, firmware modules, or other components or executable instructions. Various modules are illustrated conceptually in FIG. 2 as blocks, but some of these modules are understood to include one or more sequences of steps carried out on controller 225, such as by executing stored microcode or other instructions.

Controller 225 receives one or more signals from ventricular sensing circuit 210 that include information about sensed ventricular events. Based on sensed events, among other things, portions of the algorithms executed by controller 225 determine timing of delivering pacing, defibrillation, or other therapy, and also determine other therapy parameters. Accordingly, controller 225 provides control signals to therapy circuit 215 for controlling the delivery of output energy or other therapy to heart 115. Such therapy includes, for example, pacing energy pulses delivered simultaneously to right and left ventricles 205A–B. In another example, such therapy includes cardioversion/defibrillation/countershock energy pulses delivered simultaneously to right and left ventricles 205A–B.

Controller 225 computes intervals between cardiac events, such as paced or sensed ventricular (right or left) events. A memory location, such as second register 235, stores a current ventricular interval. The current ventricular interval is the time between the most recently detected ventricular event, $V_n$, and an immediately preceding ventricular event, $V_{n-1}$. It is unknown whether such ventricular events are associated with right ventricle 205A or left ventricle 205B, because ventricular sensing circuit 210 interfaces to these chambers by electrodes that are electrically intercoupled. A memory location, such as first register 230, stores a previous ventricular interval. The previous ventricular interval is the time between the ventricular event, $V_{n-1}$, and an associated immediately preceding ventricular event, $V_{n-2}$.

Pattern recognition module 240 classifies each of the previous and current intervals based on their respective durations. The pattern recognition module 240 also evaluates each pair of previous and current ("previous-current") intervals based on the assigned classification, as discussed below. Pattern recognition module 240 increments, decrements, and holds a count value stored in up-down counter 245 (also referred to as a pattern counter 245) based on the evaluation of the classification assigned to the intervals. The algorithm carried out within controller 325 bases the delivery of output energy by therapy circuit 215 on, among other things, the count value of counter 245.

Controller 225 also includes a therapy delivery control module 250, which executes a therapy delivery algorithm for determining the timing and other parameters of pacing therapy, anti-tachyarrhythmia therapy such as defibrillation countershocks or anti-tachyarrhythimia pacing (ATP), or other therapy. In one embodiment, therapy delivery module 250 includes a tachyarrhythmia event counter 255 that counts short cardiac intervals for diagnosing tachyarrhythmias and triggering appropriate anti-tachyarrhythmia therapy.

Figure 3:
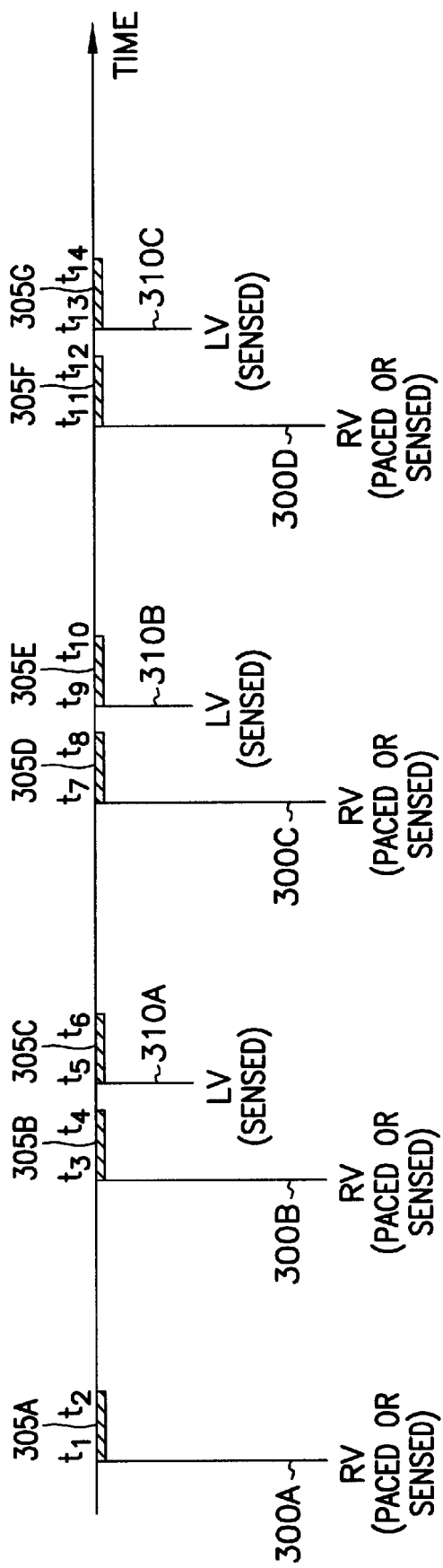
FIG. 3 illustrates generally one possible series of event markers occurring over a period of time.

FIG. 3 illustrates generally, by way of example, but not by way of limitation, one possible series of event markers occurring over a period of time. These markers represent an example of the occurrence of one possible set of events sensed by ventricular sensing circuit 210 or delivered by ventricular therapy circuit 215 over a period of time. Each event markers is described according to characteristics of the event it represents. In one example, an intrinsic right ventricular depolarization 300A at time $t_1$ results from intrinsic heart signals conducted from the right atrium, through the atrio-ventricular node, the septum, and the right ventricle. Sensed right ventricular depolarization 300A initiates a post-sense refractory period 305A, during which time sensed signals are ignored, because it is unlikely that such signals represent another ventricular depolarization during that time. The post-sense refractory period 305A expires at time $t_2$, after which time sensed signals are no longer ignored by device 105.

At time $t_3$, another intrinsic right ventricular depolarization 300B results from intrinsic heart signals conducted from the right atrium, through the atrioventricular node, the septum, and the right ventricle. Right ventricular depolarization 300B initiates another post-sense refractory period 305B, which expires at time $t_4$. In a patient with congestive heart failure, however, the same intrinsic signal that resulted in right ventricular depolarization 300B is conducted more slowly along the left side of the heart because the left side of the heart is enlarged. This results in a delayed left ventricular depolarization 310A at time $t_5$. In many patients, the delay in conduction in left ventricle 205B is long enough that the delayed left ventricular depolarization 310A occurs after expiration of the post-sense ventricular refractory period 305B. In a single-channel system, where right and left ventricular leads 110A–B, are tied together, it is possible that the delayed left ventricular depolarization 310A is mistaken for another occurrence of a right ventricular depolarization. In such a case, if device 105 erroneously computes ventricular heart rate based on the interval $t_5$–$t_3$, the computed heart rate would be extremely fast. The interval $t_5$–$t_3$ does not correspond to an interval between ventricular events occurring in the same chamber (e.g., the right ventricle), but rather, to ventricular events occurring in different chambers (e.g., the right and left ventricles).

This pattern of events can occur repeatedly, as illustrated by the subsequent event markers in FIG. 3. In such a case, intervals $t_9$–$t_7$ and $t_{13}$–$t_{11}$ also provide erroneous indications of extremely fast ventricular heart rates. These erroneous indications of a fast ventricular heart rate can result in, among other things, the inappropriate delivery of anti-tachyarrhythmia therapy. There is a need for finding some basis of distinguishing between erroneously indicated fast ventricular rates, and actual high ventricular rates. This need is particularly strong in a single channel device in which conductors and sense amplifiers are shared between left and right ventricles. In such a single-channel device, the same sense amplifier detects events from more than one chamber, and intervals between events in different chamber may be mistaken for events occurring in the same chamber.

Furthermore, device 105 should recognize and respond to the problem pattern of FIG. 3 without increasing the duration of the post-sense refractory periods 305. Extending the post-sense refractory periods 305 so that they are long enough to encompass the expected delayed left ventricular contractions would also blind device 105, for a longer period of time, to successive right ventricular senses that actually do occur at high rates. Thus, extending the post-sense refractory periods 305 may increase the time before a tachyarrhythmia is recognized and treated, or it may result in a failure to recognize and properly treat the tachyarrhythmia altogether.

One aspect of the present system recognizes a pattern among the durations of intervals between cardiac events. The system uses this pattern of interval durations to distinguish intervals concluded by delayed left ventricular contractions 310 from intervals concluded by actual right ventricular contractions 300. This allows device 105 to accurately determine heart rate based on events occurring in the same heart chamber, even when using a shared sensing circuit 210 that detects events associated with more than one heart chamber.

First, pattern recognition module 240 classifies intervals between cardiac events into at least two categories based on duration. In one example, each cardiac interval is compared to a predetermined comparison value $T_1$ such as, for example, $T_1$=500 milliseconds, or other suitable value. Intervals shorter than $T_1$ are classified as "short," and intervals longer than $T_1$ are classified as "long". In one embodiment, intervals equal to $T_1$ are included in the "short" category, however, such intervals could alternatively be included in the "long" category. In one embodiment, the value of $T_1$ is user programmable, allowing adjustment of long and short classifications to suit the needs of the particular patient.

Second, pattern recognition module 240 uses the interval classifications to distinguish successive events occurring in the same chamber from successive events occurring in different chambers, so that therapy delivery algorithms do not erroneously consider intervals between events occurring in different heart chambers as being indicative of heart rate in a single heart chamber. In one embodiment, classifications of pairs of previous and current intervals (also referred to as previous-current interval pairs) are used to remove such erroneous intervals from consideration by the therapy delivery algorithms.

Figure 4:
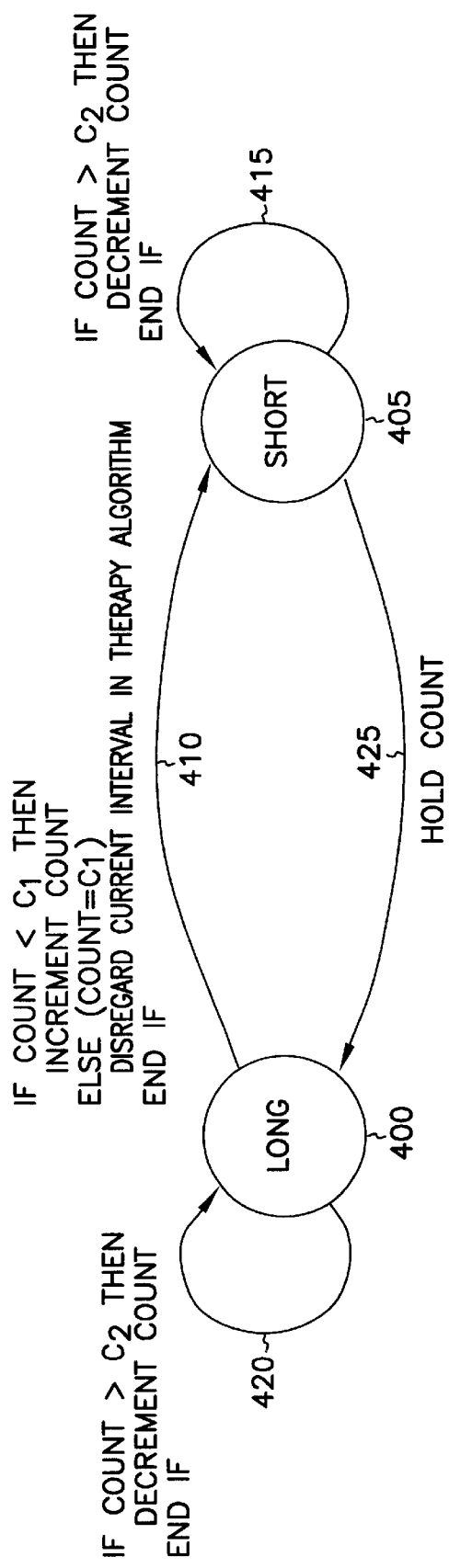
FIG. 4 is a state diagram illustrating generally one technique of controlling a counter based on classifications of intervals between cardiac events.

In one example, classifications of previous and current intervals are paired inputs used to increment, decrement, or hold the count of up-down counter 245. FIG. 4 is a state diagram illustrating generally, by way of example, but not by way of limitation, one technique of controlling counter 245 based on the classifications of previous and current intervals. FIG. 4 illustrates the states of the previous interval, i.e., a long state 400 and a short state 405. Transitions between these states are indicated by arrows, with corresponding text describing how counter 245 is affected during such transitions.

Transition 410 illustrates how counter 245 is affected if the previous interval is long and the current interval is short. For such a long-then-short previous-current interval pair, if the count value stored in counter 245 is less than a predetermined value $C_1$, such as, for example, $C_1$=3, then counter 245 is incremented. Otherwise, the count value stored in counter 245 is equal to the predetermined value $C_1$, in which case the current interval is disregarded by the therapy delivery algorithm. Stated differently, pattern recognition module 240 recognizes a long interval followed by a short interval. If a sufficient amount of long-then-short previous-current interval pairs are detected over a period of time, pattern recognition module 240 deems the current short interval as resulting not from same chamber depolarizations, but rather, as resulting from depolarizations associated with different chambers. Such a short interval is inappropriate for computing a heart rate upon which therapy delivery is based, because it does not represent a time between cardiac events occurring in the same heart chamber.

Transition 415 illustrates how counter 245 is affected if the previous and current intervals are both short. For such a short-then-short previous-current interval pair, if the count value stored in counter 245 is greater than a predetermined value $C_2$, such as, for example, $C_2=0$, then counter 245 is decremented. Otherwise, the count value stored in counter 245 is equal to the predetermined value $C_2$, and the count value of counter 245 is not modified.

Transition 420 illustrates how counter 245 is affected if the previous and current intervals are both long. For such a long-then-long previous-current interval pair, if the count value stored in counter 245 is greater than a predetermined value $C_2$, such as, for example, $C_2=0$, then counter 245 is decremented. Otherwise, the count value stored in counter 245 is equal to the predetermined value $C_2$, and the count value of counter 245 is not modified.

Transition 425 illustrates how counter 245 is affected if the previous interval is short and the current interval is long. For such a short-then-long previous-current interval pair, the count value stored in counter 245 is not changed.

Referring again to FIG. 3, in a congestive heart failure patient, there is loss of synchrony between the right and left ventricular depolarizations, due to enlargement of the left side of the heart, which results in delayed conduction of signals through the left side of the heart. As a result, the same ventricular depolarization wavefront travels more slowly through the left side of the heart than through the right side of the heart. This results in the detection of right ventricular depolarization 300B followed by an independent delayed conduction left ventricular depolarization 310A. If each interval concluded by a delayed conduction left ventricular depolarization 310 (e.g., $t_5-t_3$, $t_9-t_7$, $t_{13}-t_{11}$) is shorter than or equal to (or, alternatively, shorter than) $T_1$, then each such interval will be classified as short. If each interval concluded by a right ventricular depolarization 300 (e.g., $t_7-t_5$, $t_{11}-t_9$) is longer than (or alternatively, longer than or equal to) $T_1$, then each such interval will be classified as long.

By choosing the appropriate value of $T_1$, it is possible to discriminate between intervals concluded by right ventricular depolarizations 300 and intervals concluded by left ventricular depolarizations 310, because they are classified as long and short, respectively. Further discrimination is provided by noting that a delayed conduction left ventricular depolarization is manifested by a short interval that follows a long interval. Such a pattern is recognized by pattern recognition module 240. As described above with respect to FIG. 4, a counter is used to recognize the occurrence of this repeating pattern of long-then-short intervals. Pattern recognition module 240 increments the counter for a long-then-short previous-current interval pair, decrements the counter for a long-then-long or a short-then-short previous-current interval pair, and holds the count value for a short-then-long previous-current interval pair. By so doing, pattern recognition module 240 is capable of recognizing a number of long-then-short previous-current interval pairs occurring closely in time, before directing the therapy delivery algorithm to ignore the short current interval. However, it is understood that count value $C_1$ is programmable. For $C_1=1$ a single long-then-short previous-current interval pair is all that is needed to direct the therapy delivery algorithm to ignore the short current interval. For larger values of $C_1$, more than one long-then-short previous-current interval pair is required to ignore the short current interval. By using an up-down counter 245 and $C_1>1$, at least two successive long-then-short previous-current interval pairs is required to ignore the short current interval.

Controller 225 includes a therapy delivery control module 250, which executes a therapy delivery algorithm. In one embodiment, the therapy delivery algorithm delivers some form of anti-tachyarrhythmia therapy if a predetermined number of short intervals occur during a time period. It is understood the criteria used to classify the intervals as short for triggering delivery of anti-tachyarrhythmia therapy may be different from the criteria used for the long/short pattern recognition described above. In one embodiment, however, intervals are classified as short for determining whether anti-tachyarrhythmia therapy should be delivered using the same criteria that result in a short classification for the pattern recognition described with respect to FIG. 4.

In one example, the therapy delivery control module 250 includes a tachyarrhythmia event counter 255, such as an up-down counter, for counting the occurrences of short intervals. Thus, if the current interval is short, counter 255 is incremented, but if the current interval is not short, counter 255 is decremented or held at its previous value. If counter 255 reaches a value indicating that a sufficient number of short intervals have been detected during a desired time period, then anti-tachyarrhythmia therapy is delivered to the patient.

Using the present system, however, if the current interval is short, but is preceded by a sufficient number of long-then-short previous-current interval pairs during a period of time (such that the count value of counter 245 is equal to $C_1$), then the current interval is ignored by the therapy delivery algorithm being executed by therapy delivery control module 250, such as by not incrementing the tachyarrhythmia event counter 255. In another embodiment, the current interval is similarly ignored by portions of the therapy delivery algorithm that control the delivery of bradyarrhythmia therapy pacing energy pulses.

Figure 5:
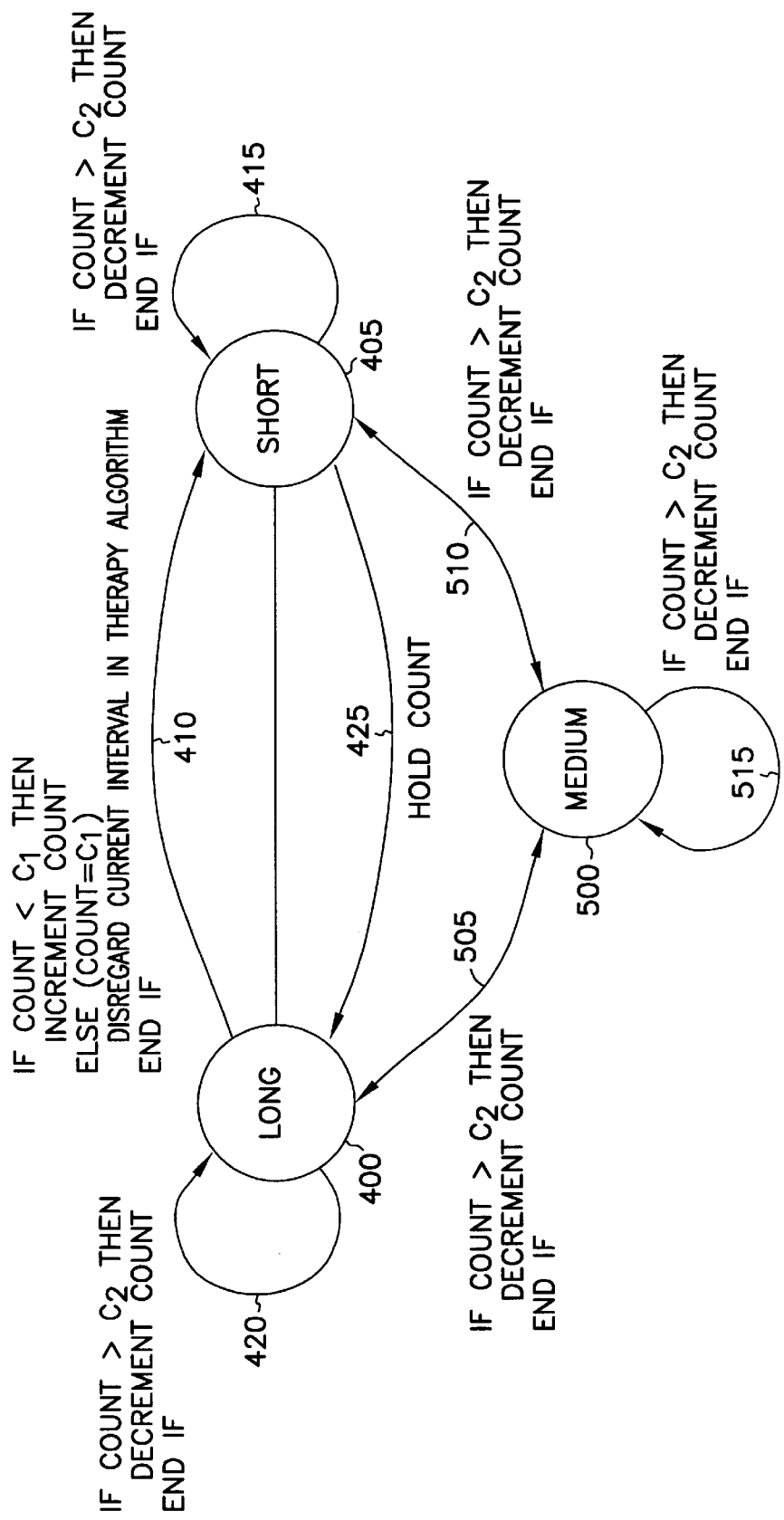
FIG. 5 is a state diagram illustrating generally another technique of controlling a counter based on classifications of intervals between cardiac events.

FIG. 5 is a state diagram, similar to FIG. 4, illustrating generally, by way of example, but not by way of limitation, another technique of controlling counter 245 based on the classifications of previous and current intervals. As illustrated in FIG. 5, more than two classifications may be used. In one embodiment, intervals are classified as either long, medium, or short by comparing the interval to predetermined comparison values $T_1$ and $T_2$, where $T_2>T_1$. Intervals shorter than $T_1$ are classified as "short," intervals longer than $T_2$ are classified as "long," and intervals longer than $T_1$ but shorter than $T_2$ are classified as "medium." In one embodiment, intervals equal to $T_1$ are included in the "short" category and intervals equal to $T_2$ are included in the "long" category, however, such intervals could alternatively be included in the "medium" category. In one embodiment, the values of $T_1$ and $T_2$ are user programmable, allowing adjustment of long and short classifications to suit the needs of the particular patient.

FIG. 5 illustrates the states of the previous interval, i.e., a long state 400, a short state 405, and a medium state 500.

Transitions between these states are indicated by arrows, with corresponding text describing how counter 245 is affected during such transitions. Transitions involving only the long state 400 or short state 405 are as described above with respect to FIG. 4. Transition 505 illustrates how counter 245 is affected for both long-then-medium and medium-then-long previous-current interval pairs. Transition 510 illustrates how counter 245 is affected for both medium-then-short and short-then-medium previous-current interval pairs. Transition 515 illustrates how counter 245 is affected for a medium-then medium previous-current interval pair. For each of transitions 505, 510, and 515, if the count value stored in counter 245 is greater than a predetermined value $C_2$, such as, for example, $C_2=0$, then counter 245 is decremented. Otherwise, the count value stored in counter 245 is equal to the predetermined value $C_2$, and the count value of counter 245 is not modified.

Figure 6:
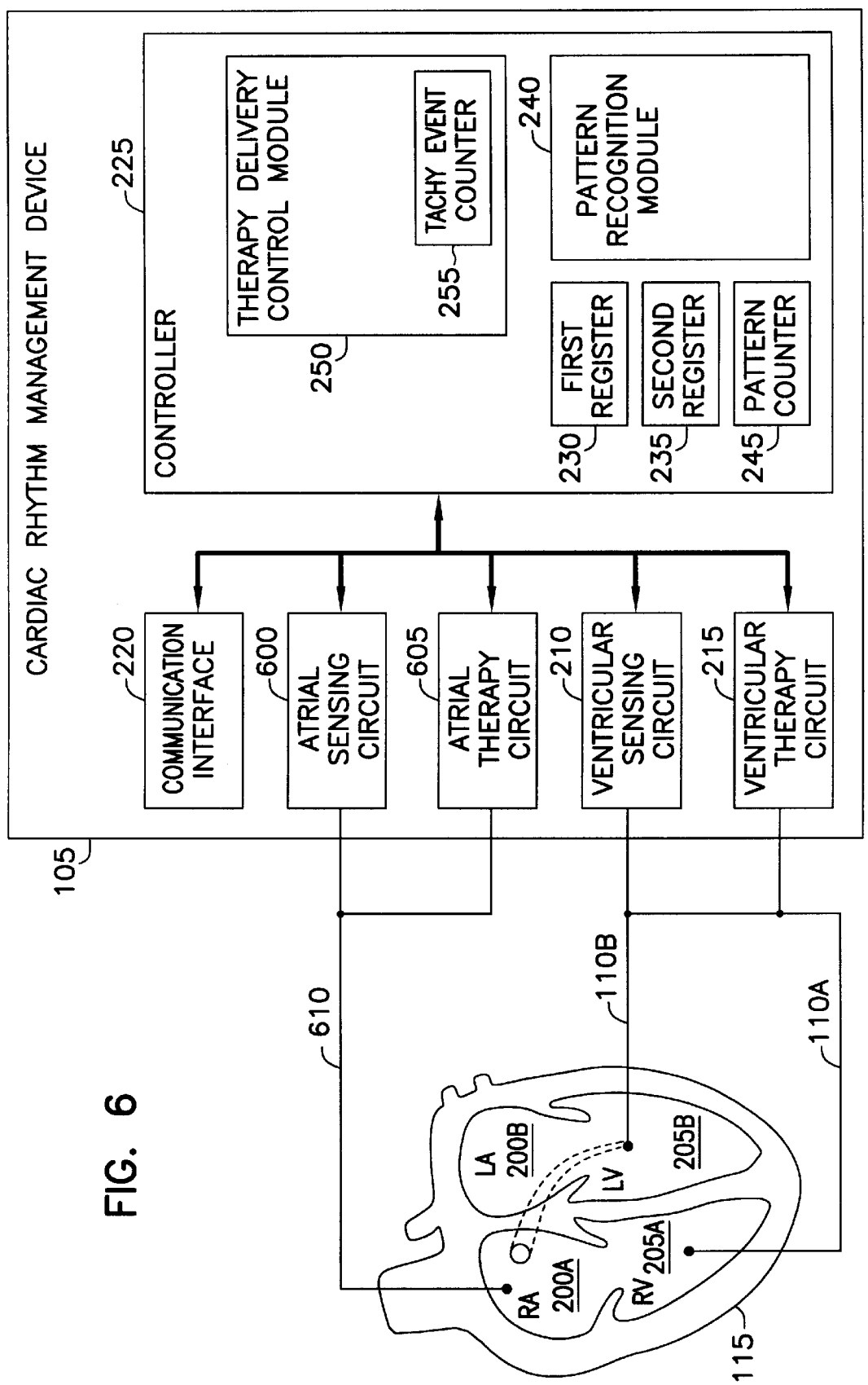
FIG. 6 is a schematic drawing illustrating generally another embodiment of portions of a cardiac rhythm management device providing atrial and biventricular operation.

FIG. 6 is a schematic drawing, similar to FIG. 2, illustrating generally, by way of example, but not by way of limitation, another embodiment of portions of device 105 including an atrial sensing circuit 600 and an atrial therapy circuit 605 coupled by lead 610 to right atrium 200A for sensing signals or delivering stimulations or countershocks. FIG. 6 illustrates that the techniques described above can provide cardiac rhythm management therapy in first and second heart chambers (e.g., right atrium 200A and right ventricle 205A), operating in any of the conventional dual-chamber pacing modes, in combination with sensing and therapy in a third heart chamber (e.g., left ventricle 205B) provided by circuits shared between the second and third heart chambers. Such pacing therapy may also be combined with anti-tachyarrhythmia therapy (such as anti-tachyarrhythmia pacing or a countershock) delivered to right atrium 200A, right ventricle 205A, and left ventricle 205B.

Figure 7:
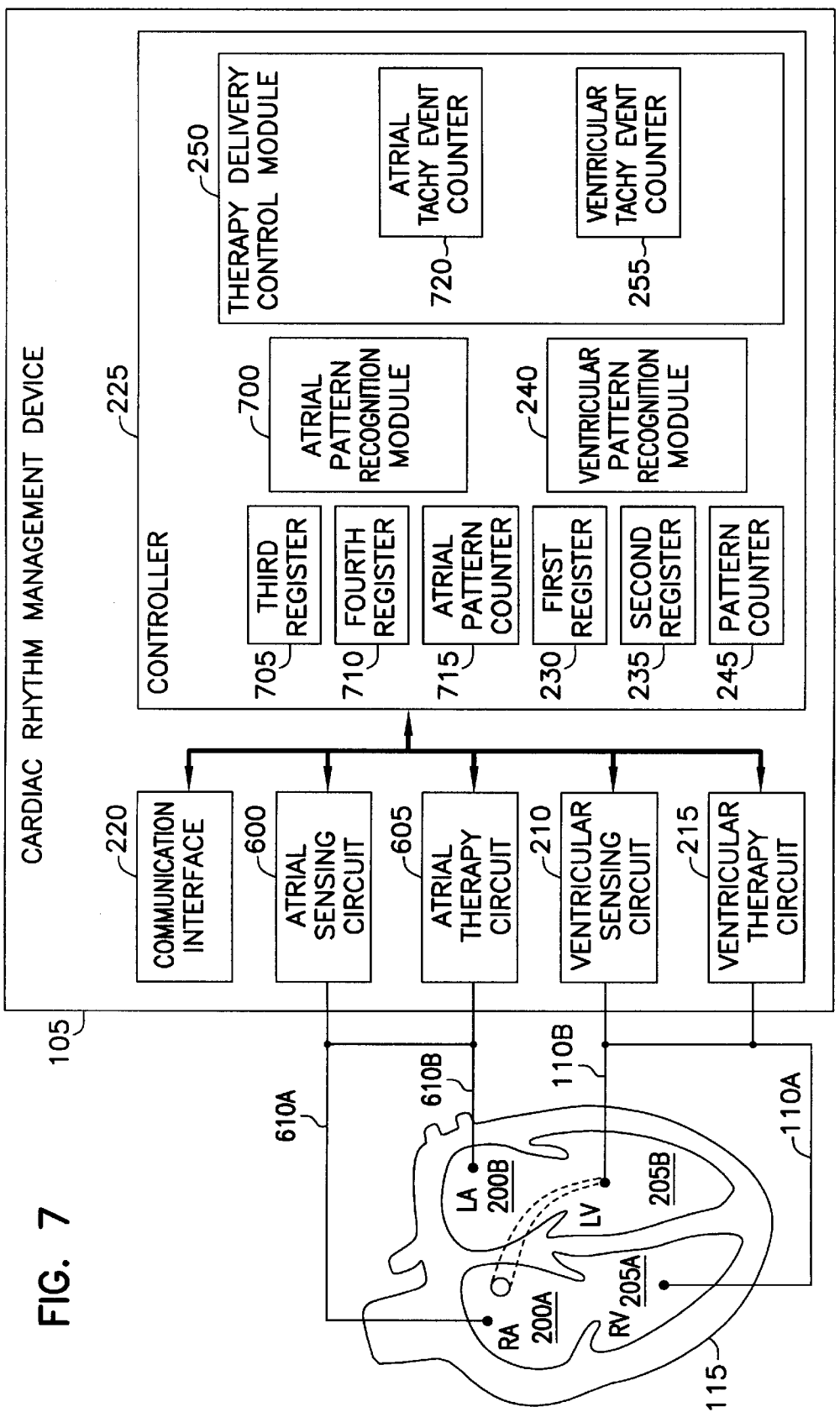
FIG. 7 is a schematic drawing illustrating generally a further embodiment of portions of a cardiac rhythm management device providing biatrial and biventricular operation.

FIG. 7 is a schematic drawing, similar to FIG. 6, illustrating generally, by way of example, but not by way of limitation, another embodiment of portions of device 105 including an atrial sensing circuit 600 and atrial therapy circuit 605 that are shared between regions associated with right atrium 200A and left atrium 200B, to which they are coupled by electrically interconnected leads 610A and 610B, respectively. FIG. 7 illustrates that the techniques described above can also provide cardiac rhythm management therapy in first and second heart chambers (e.g., right atrium 200A and right ventricle 205A) operating in any of the conventional dual-chamber pacing modes, in combination with sensing and therapy in third and fourth heart chambers (e.g., left ventricle 205B and left atrium 200B) provided by circuits shared between the first and fourth (e.g., atria 200) heart chambers and the second and third (e.g., ventricles 205) heart chambers. Such pacing therapy may be combined with anti-tachyarrhythmia therapy (such as anti-tachyarrhythmia pacing or a countershock) delivered to any of the heart chambers. In FIG. 7, the techniques discussed above for distinguishing between ventricular events using pattern recognition are also used for distinguishing between atrial events. In this embodiment, device 105 includes a separate atrial pattern recognition module 700, with associated third register 705, fourth register 710, and atrial pattern counter 715, which operate as described above with respect to the ventricles. Similarly, therapy delivery control module 250 includes an atrial tachy event counter 720 that ignores the current interval when so directed by atrial pattern recognition module 700, as described above for the ventricles.

Conclusion

The above-described system provides, among other things, cardiac rhythm management system that recognizes patterns of interval durations, allowing it to distinguish between events occurring in different heart chambers, even though signals associated with those different heart chambers are processed using a commonly shared sensing circuit. The pattern recognition techniques allow the therapy delivery algorithms to ignore intervals between cardiac events occurring in different heart chambers when determining a cardiac rate upon which the delivery of therapy is based. This reduces the risk of inappropriate delivery of therapy to the patient. For example, delayed conduction left ventricular beats are not erroneously recognized as a subsequent right ventricular beat, preventing such short intervals from inappropriately triggering a defibrillation countershock.

The above description is intended to be illustrative, and not restrictive. Many other embodiments will be apparent to those of skill in the art upon reviewing the above description. For example, the physiology of the heart may result in a right ventricular contraction that is delayed from a left ventricular contraction. By interchanging the roles of the right and left ventricular events in FIG. 3, for example, the above-described techniques can still be used to distinguish between intervals concluded by right ventricular events and intervals concluded by left ventricular events. Also, FIG. 3 was described primarily in terms of sensed right ventricular events 300. However, such right ventricular events 300 could also include paced events, such as where a pace is simultaneously delivered to the ventricles 205, but fails to capture left ventricle 205B, resulting in a delayed conduction sensed left ventricular event 310.

Moreover, although the therapy delivery algorithms were described above as ignoring the current cardiac interval if the pattern recognition criteria are met, in an alternate embodiment, ignoring the current cardiac interval includes adding the time of the current cardiac interval to the time of the next cardiac interval. For example, if the period $t_5-t_3$ of FIG. 3 is ignored, in one embodiment, the time $t_5-t_3$ is added to the time $t_7-t_5$ in computing the duration of the next cardiac interval. This recomputation of the next cardiac interval can be used, among other things, by the therapy delivery control module for computing a heart rate upon which therapy delivery is based. For example, in one embodiment, when the current interval is $t_9-t_7$, a recomputed previous interval of $t_7-t_3$ is used rather than a previous interval of $t_7-t_5$, as described above.

Also, the pattern recognition was described above as classifying the current interval, with the interval retaining its same classification when the current interval is then stored as the previous interval. Alternatively, a separate classification is performed for the previous interval, allowing for the possibility of different interval classification criteria for the previous interval, and reclassification of the current interval when it is stored as the previous interval. Such reclassification may be particularly useful in an embodiment using a recomputed previous interval, as described in the previous paragraph.

Moreover, the controller 225 was described above as storing the interval duration in the first register 230 and second register 235. However, it is understood that in an alternate embodiment, other information is stored in the first register 230 and second register 235, such as a code representing the classification (e.g., long, short, or medium) of the interval. Also, first register 230 and second register 235 could be combined with each other, or with another memory location; they are illustrated separately for conceptual clarity.

Furthermore, the pattern recognition techniques were described above, for illustrative purposes, using an algorithmic approach. It is understood that the same techniques could alternatively be implemented using a neural network. The scope of the invention should, therefore, be determined with reference to the appended claims, along with the full scope of equivalents to which such claims are entitled.

What is claimed is:

1. A method including:
   (a) computing a current interval between successive cardiac events obtained from a commonly shared first sensing channel that is coupled to two different heart chambers on different sides of a heart to detect the events occurring in at least one of (1) both right and left ventricles, and (2) both right and left atria;
   (b) classifying each of a previous and the current intervals as "long" if the interval is longer than a first duration, and as "short" if the interval is shorter than the first duration;
   (c) incrementing a counter value, if the previous interval is long and the current interval is short and the counter value is less than a maximum counter value;
   (d) decrementing the counter value, if the counter value exceeds a minimum counter value and either (1) the previous interval is long and the current interval is long, or (2) the previous interval is short and the current interval is short;
   (e) leaving the counter at its existing value, if either (1) the previous interval is long and the current interval is long, or (2) the previous interval is short and the current interval is short; and
   (f) determining timing of delivery of therapy based on intervals between cardiac events, but ignoring the current interval if the counter value is equal to the maximum counter value.

2. The method of claim 1, further including (g) storing the current interval as the previous interval and repeating steps (a)–(f).

3. The method of claim 1, in which (b) includes one of (1) classifying each of the previous and current intervals as "long" if the interval is equal to the first duration, or (2) classifying each of the previous and current intervals as "short" if the interval is equal to the first duration.

4. A method including:
   (a) computing a current interval between successive cardiac events obtained from a commonly shared first sensing channel that is coupled to two different heart chambers on different sides of a heart to detect the events occurring in at least one of (1) both right and left ventricles, and (2) both right and left atria;
   (b) classifying each of a previous and the current intervals as "long" if the interval is longer than a first duration, and as "short" if the interval is shorter than a second duration that is shorter than the first duration, and as "medium" if the interval is between the first and second durations;
   (c) incrementing a counter value, if the previous interval is long and the current interval is short and the counter value is less than a maximum counter value;
   (d) decrementing the counter value, if the counter value exceeds a minimum counter value and either (1) the previous interval is long and the current interval is long, or (2) the previous interval is short and the current interval is short, or (3) the previous interval is short and the current interval is medium, or (4) the previous interval is medium and the current interval is short, or (5) the previous interval is long and the current interval is medium, or (6) the previous interval is medium and the current interval is long, or (7) the previous interval is medium and the current interval is medium;
   (e) leaving the counter at its existing value, if either (1) the previous interval is long and the current interval is long, or (2) the previous interval is short and the current interval is short; and
   (f) determining timing of delivery of therapy based on intervals between cardiac events, but ignoring the current interval if the counter value is equal to the maximum counter value.

5. The method of claim 4, further including (g) storing the current interval as the previous interval and repeating steps (a)–(f).

6. The method of claim 4, in which (b) includes one of (1) classifying each of the previous and current intervals as "long" if the interval is equal to the first duration, or (2) classifying each of the previous and current intervals as "medium" if the interval is equal to the first duration.

7. The method of claim 4, in which (b) includes one of (1) classifying each of the previous and current intervals as "short" if the interval is equal to the second duration, or (2) classifying each of the previous and current intervals as "medium" if the interval is equal to the second duration.

* * * * *